United States Patent [19]

Tissington et al.

[11] 4,382,894
[45] May 10, 1983

[54] PRODUCTION OF α-CYANOBENZYL ESTERS

[75] Inventors: Peter Tissington; Rodney M. Giddings; Michael T. Pearse, all of Grimsby, England

[73] Assignee: Ciba-Geigy Corporation, Ardsley, N.Y.

[21] Appl. No.: 276,113

[22] Filed: Jun. 22, 1981

[51] Int. Cl.³ ............................................. C07C 121/75
[52] U.S. Cl. ................................................. 260/465 D
[58] Field of Search ..................................... 260/465 D

[56] References Cited

U.S. PATENT DOCUMENTS 4,254,050 3/1981 Baum .............................. 260/465 D

FOREIGN PATENT DOCUMENTS 24588 6/1980 European Pat. Off. .
1540632 2/1977 United Kingdom .

*Primary Examiner*—Dolph H. Torrence
*Attorney, Agent, or Firm*—Karl F. Jorda

[57] ABSTRACT

α-Cyanobenzyl esters of the general formula (I)

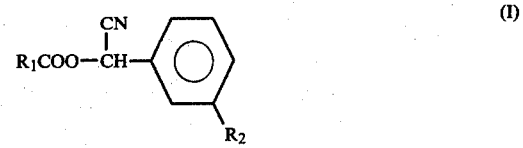

wherein $R_1$ is an optionally substituted alkyl or cycloalkyl group and $R_2$ is phenoxy, phenylthio or benzyl, are prepared by reacting a benzaldehyde of general formula (II)

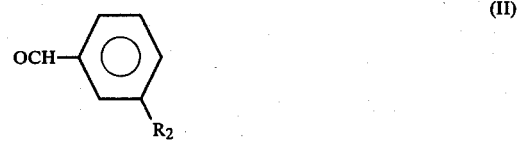

an acid halide of the general formula (III)

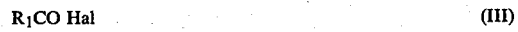

with an excess of a water soluble cyanide in a reaction medium comprising water and a substantially water-immiscible inert organic solvent in the presence of from 20 to 5000 ppm based on the weight of acid halide of formula (III), of a tertiary amine.

10 Claims, No Drawings

PRODUCTION OF α-CYANOBENZYL ESTERS

The present invention relates to the production of -cyanobenzyl esters and, in particular, to the production of -cyanobenzyl esters of substituted alkyl and substituted cycloaokyl carboxylic acids.

It is known that esters of this type can be prepared by the reaction of the appropriate carbonyl chloride with a 3-substituted benzaldehyde in the presence of aqueous sodium or potassium cyanide.

European Patent Application No. 0024588 describes a process for producing substituted (cyclo) alkylcarboxylic acid (α-cyano-3-phenoxy-benzyl) esters of the formula:

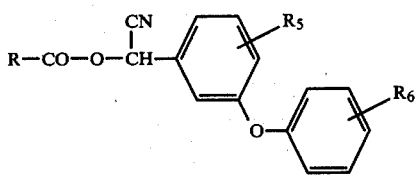

in which R is a substituted alkyl or cycloalkyl radical and $R_5$ and $R_6$ are hydrogen or halogen by reacting an acid chloride

with an aldehyde

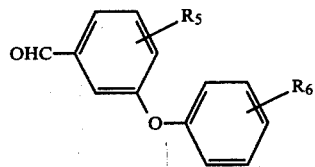

and a water soluble cyanide in a reaction medium of water and a water immiscible solvent at a temperature between 0° and 80° C.

High yields of product in short reaction times are exemplified using, as the aldehyde, 3-phenoxy-4-fluorobenzaldehyde. However, when benzaldehydes are used which do not contain a fluorine atom the reaction time needed to produce a high yield is much longer, times of 20 hours and more being required.

A similar process using a phase transfer catalyst to produce esters from aldehydes of the formula

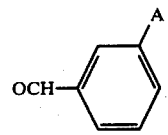

where A is phenoxy, phenylthio or benzyl, is described in British Patent Specification No. 1540632.

We have now surprisingly found that by the use of tertiary amines in much smaller amounts than are needed for known catalysts, the reaction is catalysed and goes to completion in a much shorter time than in the absence of catalyst.

Accordingly the present invention provides a process for the production of α-cyanobenzyl esters of the general formula (I)

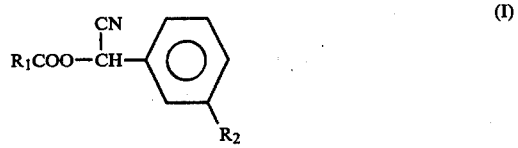

wherein $R_1$ is an optionally substituted alkyl or cycloalkyl group and $R_2$ is phenoxy, phenylthio or benzyl which comprises reacting substantially equimolar amounts of a benzaldehyde of the general formula (II)

wherein $R_2$ is as defined above, and an acid halide of the general formula (III)

wherein $R_1$ is as defined above and Hal represents chlorine or bromine with an excess of a water soluble cyanide in a reaction medium comprising water and a substantially water-immiscible inert organic solvent in the presence of from 20 to 5000 ppm, based on the weight of acid halide of formula (III), of a tertiary amine.

The tertiary amine may be a trialkylamine or a heterocyclic compound. The trialkylamine may be a compound of the formula $R_3R_4R_5N$ where $R_3$ is an alkyl group with 1 to 18 carbon atoms and $R_4$ and $R_5$ are alkyl groups with 1 to 6 carbon atoms, provided that not more than two of $R_3$, $R_4$ and $R_5$ have more than 4 carbon atoms. When the tertiary amine is a heterocyclic compound it may be derived from such compounds as pyridine and morpholine.

Examples of suitable tertiary amines are trimethylamine, triethylamine, tri-n-butylamine, n-hexyl-dimethylamine, n-octyl-dimethylamine, n-dodecyldimethylamine, n-octadecyl dimethylamine, pyridine, picoline, lutidine and N-methylmorpholine. Preferably the tertiary amine is pyridine or a dimethyl alkylamine. The preferred dimethyl alkylamine is trimethylamine.

The amount of catalyst used may be from 20 to 5000 ppm by weight, based on the weight of acid halide, preferably from 100 to 1000 ppm and most preferably from 100 to 500 ppm. If more than 5000 ppm is used there is a tendency for by-products to form, thereby causing too much aldehyde to remain unreacted and amounts above this level do not give any further advantage in increased reaction time. If less than 20 ppm is used, the reaction time becomes much longer and complete reaction becomes difficult to achieve. We have found that when using 500 ppm, yields of over 95% of high purity product can be obtained in about 4 hours.

The radical $R_2$ in general formulae (I) and (II) is preferably phenoxy or benzyl, but most preferably is phenoxy.

The group $R_1$ in general formulae (I) and (III) may be a straight or branched chain alkyl group having 1 to 10 carbon atoms, such as isopropyl, tertiary butyl and sec-butyl groups.

Suitable substituents on alkyl group $R_1$ include alkoxy, aryloxy and substituted phenyl groups, e.g. chlorophenyl groups.

Thus the acid halide of formula III may be, e.g. a 2-methylpropanoyl halide, a 2,2-dimethylpropanoyl halide or a 2-(4-chlorophenyl)-3-methyl butanoyl halide.

The group $R_1$ in general formulae (I) and (III) may be a cycloalkyl radical having 3 to 6 carbon atoms which is optionally substituted by one or more alkyl, alkenyl or haloalkenyl groups, each of which may contain up to 8 carbon atoms. The cycloalkyl group may be a cyclopropyl, cyclobutyl or cyclohexyl group, preferably cyclopropyl.

Suitable substituents on cycloalkyl group $R_1$ are methyl, ethyl, propyl, butyl, octyl, vinyl, dichlorovinyl, dibromovinyl and dimethylvinyl.

Thus the acid halide of formula (III) may be a 2,2,3,3-tetramethylcyclopropane carbonyl halide, a 2-(2',2'-dichlorovinyl)-3,3-dimethylcyclopropane carbonyl halide, a 2-(2',2'-dibromovinyl)-3,3-dimethylcyclopropane carbonyl halide or a 2-(2',2'-dimethylvinyl)-3,3-dimethylcyclopropane carbonyl halide.

Preferably the acid chlorides are used in all cases.

The molar ratio of aldehyde to acid chloride is preferably about 1:1, although a small excess of up to about 10% of either compound can be used, if desired.

The water soluble cyanide is preferably an alkali metal or alkaline earth metal cyanide, such as sodium or potassium cyanide.

The molar ratio of cyanide to aldehyde (or acid chloride) may be from 1.05:1 to 2:1, preferably from 1.1:1 to 1.8:1, and more preferably from 1.1:1 to 1.5:1. In general, we have found that the more cyanide is used, the less catalyst is needed, and vice-versa, within the above-mentioned ranges.

The amount of water used may be enough to form a saturated or unsaturated solution of the cyanide needed for the reaction, or less water than will dissolve all the cyanide needed for the reaction may be used.

The amount of water used is preferably at least the same weight as the weight of cyanide calculated as sodium cyanide, and preferably less than the amount of organic solvent, by volume. In the absence of water, complete reaction does not occur.

A wide range of water-immiscible solvents may be used in the process of the invention without unduly affecting the catalytic action of the tertiary amines.

Suitable water immiscible solvents are the liquid alkanes, cycloalkanes, aromatic hydrocarbons, chlorinated hydrocarbons and ethers, for example, n-hexane, n-heptane, n-octane, cyclohexane, benzene, toluene, xylene, chlorobenzene, methylene chloride, chloroform, carbon tetrachloride, tetrachloroethylene, trichloroethylene, 1,2-dichloroethane and diethyl ether. The preferred solvent is cyclohexane.

The reaction may be carried out at temperatures from 0° C. to 50° C., preferably from 15° C. to 25° C. The process is conveniently carried out at ambient temperature.

The invention is illustrated by the following Examples:

EXAMPLES 1–12

Preparation of α-cyano-3-phenoxybenzyl 2-(2',2'-dichlorovinyl)-3,3-dimethylcyclopropanecarboxylate A 500 ml. round-bottomed flask equipped with a stirrer operating at 500 rpm was charged with 0.2 mole of 3-phenoxybenzaldehyde, 20 ml. of water, 15.2 g. of sodium cyanide, 90 ml. of cyclohexane and a catalyst (if any). 0.2 mole of 2-(2',2'-dichlorovinyl)-3,3-dimethylcyclopropanecarbonyl chloride was added at 15°–20° over 30 minutes, followed by 10 ml. of cyclohexane. The mixture thus formed was stirred at 15°–20° C. At the end of the reaction, 100 ml. of water were added and the organic phase was filtered, washed with 100 ml. of water and the cyclohexane was then removed on a rotary evaporator. The catalysts used and the results obtained are shown in Table 1.

TABLE 1

| | CATALYST | | | |
|---|---|---|---|---|
| Example | Name | Amount wt. ppm on acid chloride | Reaction Time (hrs.) | Yield of Ester % |
| — | None | — | 8 | 88 |
| — | None | — | 17 | 91 |
| — | None | — | 40 | 96 |
| 1 | Pyridine | 100 | 19 | 97 |
| 2 | Pyridine | 500 | 8 | 99 |
| 3 | Triethylamine | 100 | 18.5 | 99 |
| 4 | Triethylamine | 500 | 8 | 94 |
| 5 | Tri-n-butylamine | 100 | 17.5 | 97 |
| 6 | Tri-n-butylamine | 500 | 8 | 95 |
| 7 | Dodecyl-dimethylamine | 100 | 17.5 | 98 |
| 8 | Dodecyl dimethylamine | 500 | 4 | 96 |
| 9 | Octadecyl dimethylamine | 500 | 8 | 95 |
| 10 | Trimethylamine | 100 | 8 | 98 |
| 11 | Trimethylamine* | 100 | 4 | 99 |
| 12 | N—methylmorpholine | 500 | 8 | 97 |

*In this example 35 ml. of water was used

EXAMPLES 13–21

The procedure described above for Examples 1–12 was repeated using different amounts of sodium cyanide, water and pyridine and different solvents as shown in Table 2, which also gives the results obtained.

TABLE 2

| Example | NaCN (moles) | Water (ml) | Solvent (100 ml) | Pyridine (ppm) | Reaction Time (hrs) | Yield % |
|---|---|---|---|---|---|---|
| — | 0.3 | 20 | Cyclohexane | 0 | 8 | 88 |
| 13 | 0.21 | 14 | Cyclohexane | 500 | 18 | 98 |
| 14 | 0.21 | 14 | Cyclohexane | 1000 | 18 | 92 |
| 15 | 0.4 | 26.7 | Cyclohexane | 1000 | 8 | 96 |
| 16 | 0.3 | 20 | Cyclohexane | 500 | 8 | 99 |
| 17 | 0.3 | 50 | Cyclohexane | 500 | 8 | 96 |
| 18 | 0.3 | 20 | Cyclohexane* | 500 | 18 | 96 |
| 19 | 0.3 | 20 | n-Hexane | 500 | 8 | 90 |
| 20 | 0.3 | 20 | Chlorobenzene | 500 | 8 | 96 |
| 21 | 0.3 | 20 | Cyclohexane | 1000 | 6 | 96 |
| — | 0.3 | 0 | Cyclohexane | 500 | 8 | 33 |

*200 ml. solvent used

EXAMPLE 22

A 500 ml round-bottomed flask equipped with a stirrer operating at 500 rpm was charged with 0.2 mole 3-phenoxybenzaldehyde, 35 ml water, 15.2 g sodium cyanide, 250 ppm trimethylamine and 100 ml cyclohexane. 0.2 mole of 2-(2',2'-dichlorovinyl)-3,3-dimethylcyclopropanecarbonyl chloride was added at 15°–20° C. over 2 hours. The mixture was stirred for a further 2 hours. The yield of α-cyano-3-phenoxybenzyl 2-(2',2'-dichlorobenzyl)-3,3-dimethylcyclopropane-carboxylate was 98%.

We claim:

1. In a process for the production of α-cyanobenzyl esters of the general formula (I)

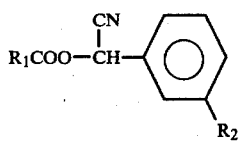

(I)

wherein $R_1$ is an optionally substituted alkyl or cycloalkyl group and $R_2$ is phenoxy, phenylthio or benzyl which comprises reacting substantially equimolar amounts of a benzaldehyde of the general formula II

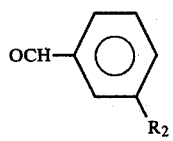

(II)

wherein $R_2$ is as defined above, and an acid halide of the general formula III $$R_1CO\ Hal \quad (III)$$

wherein $R_1$ is as defined above and Hal represents chlorine or bromine, with an excess of a water soluble cyanide in a reaction medium comprising water and a substantially water-immiscible inert organic solvent, the improvement which comprises carrying out the reaction in the presence of from 100 to 1000 ppm, based on the weight of acid halide of formula III, of pyridine.

2. The process of claim 1, wherein the amount of pyridine is from 100 to 500 ppm based on the weight of acid halide.

3. The process of claim 1, wherein the compound of formula II is phenoxy benzaldehyde.

4. The process of claim 1, wherein the compound of formula III is a halide selected from the group consisting of 2,2,3,3-tetramethylcyclopropane carbonyl halides, 2-(2',2'-dichlorovinyl)-3,3-dimethylcyclopropane carbonyl halides, 2-(2',2'-dibromovinyl)-3,3-dimethyl cyclopropane carbonyl halides, 2-(2',2'-dimethylvinyl)-3,3-dimethyl cyclopropane carbonyl halides, 2-methyl propanoyl halides, 2,2-dimethylpropanoyl halides and 2-(4-chlorophenyl)-3-methyl butanoyl halides.

5. The process of claim 1, wherein the water soluble cyanide is an alkali metal or alkaline earth metal cyanide.

6. The process of claim 1, wherein the molar ratio of cyanide to aldehyde of formula II is from 1.05:1 to 2:1.

7. The process of claim 6, wherein the molar ratio of cyanide to aldehyde is from 1.1:1 to 1.5:1.

8. The process of claim 1, wherein the amount of water used is at least the same weight as the weight of cyanide, calculated as sodium cyanide.

9. The process of claim 1, wherein the water immiscible solvent is selected from the group consisting of the liquid alkanes, cycloalkanes, aromatic hydrocarbons, chlorinated hydrocarbons and ethers.

10. The process of claim 1, wherein 3-phenoxybenzaldehyde is reacted with 2-(2',2'-dichlorovinyl)-3,3-dimethylcyclopropane-carboxylic acid chloride and sodium cyanide in a molar ratio of 1:1:1.1–1.5 in a reaction medium comprising water and cyclohexane, at a temperature from 15°–25° C. in the presence of 100 to 500 ppm of pyridine based on the weight of 2-(2',2'-dichlorovinyl)-3,3-dimethylcyclopropane carboxylic acid chloride.

* * * * *